United States Patent

Wermuth

[11] 4,134,991
[45] Jan. 16, 1979

[54] DERIVATIVES OF 2-(3-PHENYL-2-AMINOPROPIONYLOXY)-ACETIC ACID

[75] Inventor: Camille G. Wermuth, Strasbourg, France

[73] Assignee: Synthelabo, Paris, France

[21] Appl. No.: 836,724

[22] Filed: Sep. 26, 1977

[30] Foreign Application Priority Data

Sep. 28, 1976 [FR] France ................ 76 29057

[51] Int. Cl.$^2$ ............... A61K 31/24; C07C 101/20
[52] U.S. Cl. ............................ 424/309; 560/39; 560/40
[58] Field of Search ............... 560/40, 39; 424/309

[56] References Cited

U.S. PATENT DOCUMENTS

| | | | |
|---|---|---|---|
| 3,329,711 | 7/1967 | Hegediis et al. | 560/40 |
| 3,983,138 | 9/1976 | Saari | 560/40 |
| 4,051,169 | 9/1977 | Saari | 560/40 |

Primary Examiner—Bernard Helfin
Assistant Examiner—G. T. Breitenstein
Attorney, Agent, or Firm—Stevens, Davis, Miller & Mosher

[57] ABSTRACT

A compound having the general formula

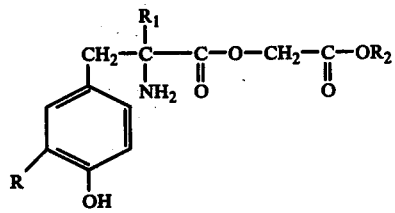

in which R represents a hydrogen atom or a hydroxyl radical, $R_1$ represents a hydrogen atom or a methyl radical, and $R_2$ represents a phenylethyl radical, a $C_1$–$C_{16}$ alkyl radical, or a $C_6$–$C_{16}$ monocyclic, polycyclic or alicyclic radical optionally bonded through a methylene radical, and its pharmaceutically acceptable acid addition salts, the formula (I) having the L-configuration when R is OH and when R and $R_1$ are both hydrogen, and having the DL-configuration when R is hydrogen and $R_1$ is methyl.

These compounds and salts are useful as medicaments in human and veterinary medicine for cardiovascular and/or neurological treatment.

10 Claims, No Drawings

DERIVATIVES OF 2-(3-PHENYL-2-AMINOPROPIONYLOXY)-ACETIC ACID

This invention relates to new derivatives of 2-(3-phenyl-2-aminopropionyloxy)-acetic acid, to their acid addition salts with pharmaceutically acceptable acids, to the preparation of these derivatives and salts, and to medicaments in which they are present as active principle.

The invention provides a compound having the general formula I

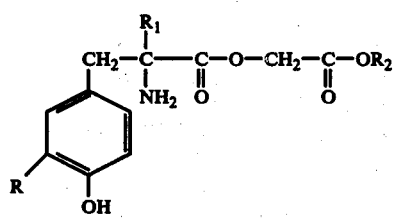

in which R represents a hydrogen atom or a hydroxyl radical, $R_1$ represents a hydrogen atom or a methyl radical, and $R_2$ represents a phenylethyl radical, a $C_1$–$C_{16}$ alkyl radical, or a $C_6$–$C_{16}$ monocyclic, polycyclic or alicyclic radical optionally bonded through a methylene radical, and its pharmaceutically acceptable acid addition salts, the formula (I) having the L-configuration when R is OH and when R and $R_1$ are both hydrogen, and having the DL configuration when R is hydrogen and $R_1$ is methyl. The derivatives of DOPA, α-methyl-DOPA and tyrosine according to the invention are derived from L-phenylalanine. The derivatives of α-methyl-tyrosine according to the invention are derived from DL-phenylalanine.

The compounds (I) are medicaments which can be used in human and veterinary therapy, especially in the cardiovascular and/or neurological area. They can be prepared by known methods and, in particular, according to the reaction scheme below:

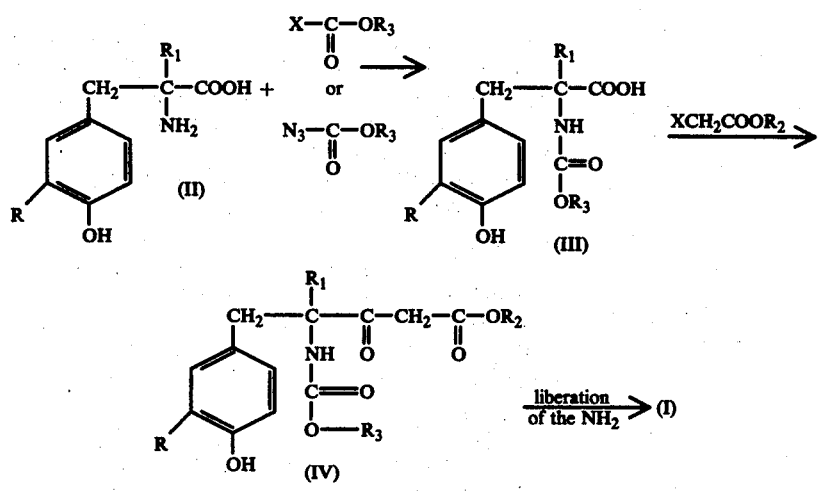

In certain methods of application, it is also desirable to block the phenolic OH group with the same removable group $R_3$—O—CO.

In the above formulae, with R, $R_1$ and $R_2$ having the same meanings as in the formula (I), X represents a halogen atom, especially chlorine or bromine, and $R_3$ represents an aliphatic or aromatic group, in particular a t-butyl or benzyl radical, which is intended to protect the amine function.

The condensation of the derivatives of α-aminophenylpropionic acid (II) with

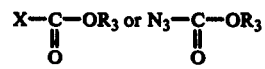

is preferably carried out in an alkaline medium at room temperature. In the case of

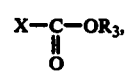

the addition of a base which is an acceptor of a hydrogen halide acid is advantageous. The condensation of the compound (III) with the halogenoacetate

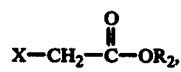

is preferably carried out in the presence of a base which is an acceptor of a halohydric acid and in an aprotic solvent such as DMF (dimethylformamide).

The conversion of the compound (IV) thus obtained into the compound (I) requires the liberation of the $NH_2$. The latter is carried out either by acid treatment (for example t-butyloxycarbonyl derivative) or by catalytic hydrogenation (for example benzyloxycarbonyl derivative).

The examples which follow illustrate the invention. The optical rotation of the compounds was determined on a 2% strength solution of the compound in 95% strength ethanol, at a temperature of 25° C.

EXAMPLE I

Lauryl L-2-[3-(3,4-dihydroxyphenyl)-2-amino-2-methylpropionyloxy]-acetate and its acid oxalate

[(I); R = OH; $R_1$ = $CH_3$; $R_2$ = $C_{12}H_{25}$; Code number SL 75-892]

(a) Benzyl chloroformate

A solution of 57.3 g (0.53 mol) of benzyl alcohol in 530 ml of anhydrous ether is cooled in an ice bath. 265 ml of a 20% strength toluene solution of phosgene (0.53 mol) are added dropwise whilst stirring magnetically.

When the addition has ended, the mixture is stirred for a further hour at ambient temperature, and is then allowed to stand for one night. The solvent is then evaporated off at a temperature not exceeding 50°. A colourless oily residue of crude benzyl chloroformate is obtained. It is used without purification for the continuation of the synthesis.

(b) L-3-(3,4-Dihydroxyphenyl)-2-methyl-2-benzyloxycarbonylaminopropionic acid 22.9 g (0.1 mol) of L-3-(3,4-dihydroxyphenyl)-2-amino-2-methylpropionic acid, 38.1 g (0.1 mol) of borax and 500 ml of water are introduced into a 2 liter Erlenmeyer flask. The mixture is stirred magnetically under a stream of nitrogen until all has dissolved, and the pH is adjusted to 9–9.5 with 2N sodium hydroxide. Benzyl chloroformate, obtained starting from 0.15 mol of benzyl alcohol, is then added over a period of 3 hours, whilst continuing the vigorous stirring. The pH of the solution is kept between 9 and 9.5 throughout this addition.

The solution is then washed twice with ether. The aqueous phase is acidified with ice-cold hydrochloric acid, which has been diluted by half, and this solution is extracted with ether. The ether extracts are combined, washed with water, dried over magnesium sulphate and evaporated to dryness.

L-3-(3,4-Dihydroxyphenyl)-2-methyl-2-benzyloxycarbonylaminopropionic acid is obtained in the form of a very viscous greenish residue which is used without purification for the continuation of the synthesis; it weighs 13.5 g (that is to say a yield of 39%).

(c) Lauryl L-2-[3-(3,4-dihydroxyphenyl)-2-benzyloxycarbonylamino-2-methylpropionyloxy]-acetate 10 g (0.029 mol) of L-3-(3,4-dihydroxyphenyl)-2-methyl-2-benzyloxycarbonylaminopropionic acid, 45 ml of dimethylformaide, 5.26 g (0.029 mol) of dicyclohexylamine, 7.6 g (0.029 mol) of lauryl chloroacetate (prepared according to A. Baniel et al, J. org. chem. 1948, 13, 791) and 250 mg of sodium iodide (catalyst) are mixed together. This mixture is stirred for 15 hours. Dicyclohexylamine hydrochloride is then removed by filtration and washed with ethyl acetate. A brown oil is collected and transferred onto a silica gel column using, as eluants, initially a mixture of ethyl acetate and hexane (2/8), and then a mixture of ethyl acetate and hexane (2.5/7.5). 12 g of lauryl L-2-[3-(3,4-dihydroxyphenyl)-2-benzyloxycarbonylamino-2-methylpropionyloxy]-acetate are obtained in the form of a pale yellow oil. (Yield 72%).

A single spot, rf 0.64.$[\alpha]_D^t = +5.4°$, is observed by thin layer chromatography (ethyl acetate - hexane 5/5).

(d) Lauryl L-2-[3-(3,4-dihydroxyphenyl)-2-amino-2-methylpropionyloxy]-acetate acid oxalate A solution of 12 g (0.021 mol) of the preceding compound in 115 ml of isopropyl alcohol is hydrogenated for 24 hours at atmospheric pressure in the presence of 2.9 g (0.023 mol) of oxalic acid and 1.2 g of 10% strength palladium on charcoal.

The catalyst is then filtered off and the residue is evaporated to dryness under reduced pressure. The solid oxalate is taken up in ether and the solution is filtered. Lauryl L-2-[3-(3,4-dihydroxyphenyl)-2-amino-2-methylpropionyloxy]-acetate acid oxalate is recrystallised 3 times from ethyl acetate containing a few drops of isopropyl alcohol.

The salt is obtained in the form of fine glossy crystals which melt at 116°. The yield is 7.7 g (that is to say 65%).

EXAMPLE 2

Tetradecyl L-2-[3-(3,4-dihydroxyphenyl)-2-aminopropionyloxy]-acetate and its hydrochloride. [(I): R = OH; $R_1$ = H; $R_2$ = $C_{14}H_{29}$ Code number SL 75-890]

In a similar way to that which has been described in Example I, the following are prepared successively: benzyl chloroformate, L-3-(3,4-dihydroxyphenyl)-2-benzyloxycarbonylaminopropionic acid, in the form of a vitreous product which is used without purification, and tetradecyl L-2-[3-(3,4-dihydroxyphenyl)-2-benzyloxycarbonylaminopropionyloxy]-acetate which melts at 68°.

(b) 29.3 g (0.05 mol) of the last compound, dissolved in 450 ml of isopropyl alcohol, are then hydrogenated for about 20 hours at atmospheric pressure in the presence of 6.65 g (0.0525 mol) of benzyl chloride and 3 g of 10% strength palladium on charcoal.

After the catalyst has been filtered off, the filtrate is evaporated to dryness under reduced pressure. The residue is taken up in ether, the solution is filtered, and the product is recrystallised several times from a mixture of isopropyl alcohol and ethyl acetate (4/6). 14.6 g of tetradecyl L-2-[3-(3,4-dihydroxyphenyl)-2-aminopropionyloxy]-acetate hydrochloride are collected in the form of white crystals which melt at 148°. Yield 60%. $[\alpha]_D^t = +4.8°$.

EXAMPLE 3 n-Tetradecyl L-2-[3-(3,4-dihydroxyphenyl)-2-amino-2-methylpropionyloxy]-acetate and its acid oxalate.

[(I): R = OH; $R_1$ = $CH_3$; $R_2$ = $C_{14}H_{29}$; Code number SL 76-863]

In a similar way to that which has been described in Examples 1 and 2, the following are prepared successively: benzyl chloroformate, L-3-(3,4-dihydroxyphenyl)-2-benzyloxycarbonylamino-2-methylpropionic acid and n-tetradecyl L-2-[3-(3,4-dihydroxyphenyl)-2-benzyloxycarbonylamino-2-methylpropionyloxy]-acetate, which is a yellow oily liquid and is obtained with a yield of 79%.

A mixture of 10 g (0.167 mol) of the last compound, 100 ml of isopropyl alcohol, 2.3 g (0.0184 mol) of oxalic acid and 1 g of 10% strength palladium on charcoal is hydrogenated for about 24 hours at atmospheric pressure.

After the catalyst has been filtered off and the filtrate evaporated to dryness, the precipitate of oxalate obtained is taken up in ether and the solution is filtered.

The product is recrystallised 3 times from ethyl acetate containing a few drops of isopropyl alcohol. 6.6 g (yield 71%) of n-tetradecyl L-2-[3-(3,4-dihydroxyphenyl)-2-amino-2-methylpropionyloxy]-acetate acid oxalate are collected as white crystals which melt at 123.5°. $[\alpha]_D^t = +5.3°$.

EXAMPLE 4

Ethyl L-2-[3-(4-hydroxyphenyl)-2-aminopropionyloxy]-acetate and its hydrochloride.

[(I): R = H; $R_1$ = H; $R_2$ = $C_2H_5$; Code number SL 75-873]

(a) t-Butyl azidoformate 60 g of t-butyloxycarbonylhydrazine are dissolved at about 30° in 48 ml of acetic acid; the solution is diluted with 72 ml of water and cooled to −2° with an ice-salt bath.

34.6 g of sodium nitrite, dissolved in 48 ml of water, are added dropwise to the mixture, whilst stirring magnetically and keeping the temperature in the region of 0°. The stirring is continued for 1 hour 30 minutes after the end of the addition, the mixture is diluted with 60 ml of water and the supernatant organic phase is decanted. The aqueous phase is extracted 3 or 4 times with pentane and these extracts are mixed with the 1st organic phase. The solution obtained is washed 5 times with 30 ml of water, 3 times with 60 ml of a N solution of potassium bicarbonate and finally 3 times with 60 ml of water. After drying over magnesium sulphate, the solvent is evaporated off at ordinary temperature.

59 g (yield 97%) of crude t-butyl azidoformate, which is used without purification, are obtained. This compound boils at 34°/12 mm Hg.

(b) The t-butyloxycarbonyl-L-tyrosine intermediate is prepared under similar conditions to those which have been described in the preceding examples. This compound is also commercially available.

(c) Ethyl L-2-[3-(4-hydroxyphenyl)-2-aminopropionyloxy]-acetate hydrochloride

A mixture of 7 g (0.025 mol) of t-butyloxycarbonyl-L-tyrosine, 4.53 g (0.025 mol) of dicyclohexylamine and 4.18 g (0.025 mol) of ethyl bromoacetate in 40 ml of dimethylformamide is stirred for 15 hours. The precipitate of dicyclohexylamine hydrobromide which has formed is filtered off and washed with ethyl acetate. The combined filtrates are evaporated to dryness under reduced pressure. An oily residue is obtained which is taken up in ethyl acetate and washed twice with a 2N solution of sulphuric acid, once with water, twice with a solution of potassium bicarbonate and, finally, once with water. After desiccation over magnesium sulphate, the solution is evaporated to dryness. An oily residue is obtained which is dissolved in 50 ml of acetic acid containing 1.8 g (0.05 mol) of gaseous hydrochloric acid. The solution is allowed to stand for 30 minutes and then evaporated to dryness under reduced pressure, and the residue is recrystallised several times from a mixture of isopropanol and ether. 5.7 g of the hydrochloride (yield 75%), which melts at 176°, are collected. $[\alpha]_D^t$ = + 12.2°.

EXAMPLE 5

Adamantyl L-2-[3-(3,4-dihydroxyphenyl)-2-amino-2-methylpropionyloxy]-acetate and its acid oxalate

[(I): R = OH; $R_1$ = $CH_3$; $R_2$ = Code number: SL 76-861].

(a) Adamantyl chloroacetate

A mixture of 24.8 g (0.22 mol) of chloroacetyl chloride and 30.4 g (0.2 mol) of 1-hydroxyadamantane is heated in an oil bath at 50°-60° until a solution is obtained.

Adamantyl chloroacetate crystallises on cooling. Ice-cold water is added to the mixture which is extracted with ether. The organic fraction is washed with water, then with a solution of potassium bicarbonate and again with water. The solution is dried and evaporated to dryness.

30.3 g of glossy white crystals are collected, which melt at 75° after one recrystallisation from the minimum amount of hexane. Yield 66%.

(b) L-3-(3,4-Dihydroxyphenyl)-2-methyl-2-benzyloxycarbonylaminopropionic acid

This compound is prepared according to the instructions in Example 1.

(c) Adamantyl L-2-[3-(3,4-dihydroxyphenyl)-2-benzyloxycarbonylamine-2-methylpropionyloxy]-acetate This compound is obtained under similar conditions to those which have been described in the preceding examples. A brown oil is obtained which is transferred onto a silica gel column, first with a mixture of hexane and ethyl acetate (8/2), and then with a mixture of hexane and ethyl acetate (7/3).

7.6 g of a fairly thick, vitreous, pale yellow compound are thus collected. The yield is 49%. $[\alpha]_D^t$ = + 8.3°.

(d) Adamantyl L-2-[3-(3,4-dihydroxyphenyl)-2-amino-2-methylpropionyloxy]-acetate acid oxalate 7.6 g (0.014 mol) of adamantyl L-2-(3,4-dihydroxyphenyl)-2-benzyloxycarbonylamino-2-methylpropionyloxy]-acetate in 80 ml of isopropyl alcohol are hydrogenated at atmospheric pressure for 24 hours in the presence of 1.95 g (0.0154 mol) of oxalic acid and 760 mg of 10% strength palladium on charcoal.

After the end of the reaction, the catalyst is filtered off and the filtrate is evaporated to dryness. The residue is taken up in ether and the solution is filtered. The compound is recrystallised 3 times from a mixture of ethyl acetate and isopropyl alcohol (6/4) to which a small amount of ether is added.

3.1 g of adamantyl L-2-[3-(3,4-dihydroxyphenyl)-2-amino-2-methylpropionyloxy]-acetate acid oxalate, which melts at 139°, are collected. Yield 45%.

EXAMPLE 6

Octyl D,L-2-[3-(4-hydroxyphenyl)-2-amino-2-methylpropionyloxy]-acetate and its hydrochloride

[(I): R = H; $R_1$ = $CH_3$; $R_2$ = n-$C_8H_{17}$; Code number SL 76-877]

(a) D,L-3-(4-Benzyloxycarbonyloxyphenyl)-2-benzyloxycarbonylamino-2-methylpropionic acid 21.5 g (0.11 mol) of D,L-α-methyltyrosine are suspended in 220 ml of water and the pH is brought to between 8 and 9 with 2N sodium hydroxide solution.

The suspension is stirred and benzyl chloroformate, obtained starting from 0.264 mol of benzyl alcohol, is added over a period of about 2 hours, whilst keeping the pH between 8 and 9 by the addition of 2N sodium hydroxide solution.

The mixture is stirred for a further 2 hours at the temperature of the laboratory.

It is acidified with hydrochloric acid, which has been partially cooled with ice, and extracted with ethyl acetate.

The ethyl acetate fractions are washed 3 times with water, dried over Mg sulphate and evaporated to dryness.

A fairly thick yellow oil is obtained which is used as it is.

(b) Octyl D,L-2-[3-(4-benzyloxycarbonyloxyphenyl)-2-benzyloxycarbonylamino-2-methylpropionyloxy]-acetate:

A mixture of 20.4 g (0.044 mol) of the product obtained above, 65 ml of dimethylformamide, 7.25 g (0.04 mol) of dicyclohexylamine, 8.3 g (0.04 mol) of octyl chloroacetate and 250 mg of Na iodide (catalyst) is stirred for 15 hours.

The dicyclohexylamine hydrochloride formed is filtered off and washed with ethyl acetate, and the filtrate is evaporated.

The residue is taken up in ethyl acetate and washed several times with water, acid, and potassium bicarbonate.

The solution is dried over Mg sulphate and evaporated to dryness.

The oily residue is transferred onto a silica gel column with a mixture of ethyl acetate and hexane. A colourless oil is obtained.

(c) Octyl D,L-2-[3-(4-hydroxyphenyl)-2-amino-2-methylpropionyloxy]-acetate hydrochloride:

A mixture of 16.6 g (0.0262 mol) of the compound obtained above, 145 ml of isopropyl alcohol, 3.5 g (0.0275 mol) of benzyl chloride and 2.5 g of 10% strength palladium on charcoal is hydrogenated at atmospheric pressure for 24 hours.

The catalyst is filtered off and the filtrate is evaporated to dryness. The hydrochloride is taken up in ether and the solution is filtered.

White crystals are obtained after recrystallisation from a mixture of ethyl acetate and isopropanol.

Melting point (Mettler) = 169° C.

In Table (I) below, the properties of the exemplified compounds, and of similar compounds preparable by analogous methods, are summarized. The analyses and IR and NMR spectra confirm the structure of the compounds.

Table (I)

| Compound No. | Code No. | R | $R_1$ | $R_2$ | Characteristics Melting point in ° C | |
|---|---|---|---|---|---|---|
| 1 (Example 1) | SL 75-892 | OH | $CH_3$ | $C_{12}H_{25}$ | Acid oxalate | m.p.: 116 |
| 2 (Example 2) | SL 75-890 | OH | H | $C_{14}H_{29}$ | Hydrochloride | m.p.: 148 |
| 3 (Example 3) | SL 76-863 | OH | $CH_3$ | $C_{14}H_{29}$ | Acid oxalate | m.p.: 123.5 |
| 4 (Example 4) | SL 75-873 | H | H | $C_2H_5$ | Hydrochloride | m.p.: 176 |
| 5 (Example 5) | SL 76-861 | OH | $CH_3$ | adamantyl | Acid oxalate | m.p.: 139 |
| 6 | SL 75-855 | OH | H | $C_2H_5$ | Hydrochloride | m.p.: 173 |
| 7 | SL 75-856 | OH | H | n-$C_8H_{17}$ | Hydrochloride | m.p.: 155 |
| 8 | SL 75-857 | OH | H | n-$C_{12}H_{25}$ | Hydrochloride | m.p.: 146 |
| 9 | SL 75-858 | OH | H | n-$C_{16}H_{33}$ | Hydrochloride | m.p.: 146 |
| 10 | SL 75-874 | H | H | n-$C_8H_{17}$ | Hydrochloride | m.p.: 168 |
| 11 | SL 75-875 | H | H | n-$C_{12}H_{25}$ | Hydrochloride | m.p.: 164 |
| 12 | SL 75-876 | H | H | n-$C_{16}H_{33}$ | Hydrochloride | m.p.: 168 |
| 13 | SL 75-888 | OH | H | n-$C_{11}H_{23}$ | Hydrochloride | m.p.: 151 |
| 14 | SL 75-889 | OH | H | n-$C_{13}H_{27}$ | Hydrochloride | m.p.: 149 |
| 15 | SL 75-891 | OH | $CH_3$ | $C_2H_5$ | Neutral oxalate | m.p.: 146 |
| 16 | SL 75-893 | OH | $CH_3$ | n-$C_{16}H_{33}$ | Acid oxalate | m.p.: 124 |
| 17 | SL 75-899 | OH | H | n-$C_{10}H_{11}$ | Hydrochloride | m.p.: 154 |
| 18 | SL 75-900 | OH | H | $-CH_2-CH_2-C_6H_5$ | Hydrochloride | m.p.: 173 |
| 19 | SL 75-904 | OH | $CH_3$ | n-$C_8H_{17}$ | Acid oxalate | m.p.: 114 |
| 20 | SL 76-859 | OH | $CH_3$ | $-CH_2-C(CH_3)_2-CH_3$ with $CH_3$ | Acid oxalate | m.p.: 135 |
| 21 | SL 76-860 | OH | $CH_3$ | n-$C_6H_{13}$ | Acid oxalate | m.p.: 118 |
| 22 | SL 76-862 | OH | $CH_3$ | $-CH(CH_3)-(CH_2)_9-CH_3$ | Acid oxalate | m.p.: 111 |
| 23 | SL 76-864 | OH | $CH_3$ | $-CH_2$-cycloheptyl | Acid oxalate | m.p.: 155 |
| 24 | SL 76-875 | OH | $CH_3$ | n-$C_{13}H_{27}$ | Acid oxalate | m.p.: 115 |
| 25 | SL 76-876 | OH | $CH_3$ | n-$C_{15}H_{31}$ | Acid oxalate | m.p.: 120.5 |
| 26 | SL 77-856 | OH | $CH_3$ | adamantylmethyl | Acid oxalate | m.p.: 176 |
| 27 | SL 77-857 | OH | $CH_3$ | (−)bornyl | Acid oxalate | m.p.: 156 |
| 28 | SL 77-14 858 | OH | $CH_3$ | (+)isobornyl | Acid oxalate | m.p.: 158 |
| 29 (Example 6) | SL 76-877 | H | $CH_3$ | n-$C_8H_{17}$ | Hydrochloride | m.p.: 169 |
| 30 | SL 76-878 | H | $CH_3$ | n-$C_{12}H_{25}$ | Hydrochloride | m.p.: 155 |

These compounds have been subjected to pharmacological tests which have shown their valuable properties in neurological and cardiovascular areas, and it has been verified that the toxicity of the products of this series is low, in particular when administered orally.

The compounds (I), for which R represents OH and $R_1$ represents H, have a high activity against catalepsy caused by morphine in the Sprague-Dawley male rats. By way of example, the AD 50 (50% active doses) (determined by intraperitoneal administration) of SL 75-857 and SL 75-890 are 300 mg/kg, whilst that of L-3,4-dihydroxyphenylalanine or L-DOPA, chosen as a reference substance, is 600 mg/kg under the same experimental conditions. The compounds (I), for which R represents H and $R_1$ represents $CH_3$, in particular the compounds SL 76-877 and 76-878, are more active than α-methyltyrosine methyl ester as far as the reduction of cerebral catecholamine is concerned. The compounds (I), for which R represents OH and $R_1$ represents H, and those, for which R is H and $R_1$ is $CH_3$, can be used especially in the treatment of Parkinson's disease. They may be presented in any customary form which is appropriate for oral administration (tablets, dragees, gelatin-coated pills, capsules, cachets, solutions or suspensions to be taken orally) and may contain, for example, 0.100 to 0.800 g per unit dosage, the daily dose being from 0.100 to 8 g.

The compounds (I), for which R represents OH and $R_1$ represents $CH_3$ or for which R and $R_1$ both represent H, have shown themselves to be effective central antihypertensive agents. The studies were carried out on genetically hypertensive Okamoto or Charles River male rats. The products lower the systolic arterial blood pressure without any notable effect on the cardiac frequency. Two hours after administration of the compounds studied, at a dose of 50 mg/kg, the systolic pressure was 20 to 66% lower, and was still 15 to 54% lower after 24 hours. The most active products are the compounds SL 75-892, SL 76-863 and SL 76-861. In Table (II) below, the results obtained for these three compounds are indicated in comparison with α-methyl-DOPA.

The compounds (I), for which R represents OH and $R_1$ represents $CH_3$ or for which R and $R_1$ both represent H, can be used in the treatment of various forms of hypertension. Their presentation is similar to that indicated for the compounds for which R = OH and $R_1$ = H but, in this case, the daily dosage is in general lower: from 0.100 g to 5 g per day. Their extremely prolonged action makes it possible to reduce the frequency of administration.

The preferred method of administration is oral administration; however, the compounds (I) can also be presented in forms which are suitable for endorectal or parenteral administration.

TABLE (II)

| COMPOUND | DOSE mg/kg administered intraperitoneally | Number of animals | Pressure CONTROL VALUE (mm Hg) | 3 HOURS Δ (mm Hg) | 3 HOURS Δ% | 24 HOURS Δ (mm Hg) | 24 HOURS Δ% |
|---|---|---|---|---|---|---|---|
| Placebo | — | 5 | 205 ± 10.7 | − 9 ± 5.6 |  | + 1 ± 2.9 |  |
| α-Methyl-Dopa | 50 | 5 | 200 ± 6.3 | − 14 ± 10.6 | −7 | − 7 ± 8.9 | − 4 |
| SL 75-892 | 50 | 5 | 197 ± 3.0 | − 28 ± 8.1 | −14 | − 15 ± 9.0 | − 8 |
| SL 76-861 | 50 | 5 | 197 ± 2.6 | − 61 ± 10.4 | −31 | − 46 ± 15.6 | − 23 |
| SL 76-863 | 50 | 5 | 207 ± 4.4 | − 19 ± 5.6 | −9 | − 23 ± 8.9 | − 11 |

I claim:

1. A compound of the formula

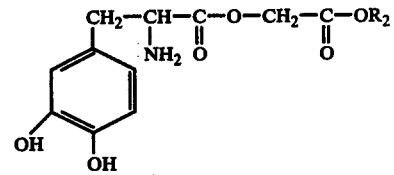

wherein $R_2$ is a phenylethyl or $C_1$–$C_{16}$ alkyl, or a pharmaceutically acceptable acid addition salt thereof.

2. A compound of claim 1 in the L-configuration.

3. A compound of claim 1 wherein $R_2$ is alkyl of 8 to 16 carbon atoms, or a pharmaceutically acceptable acid addition salt thereof.

4. A compound of claim 3 wherein $R_2$ is alkyl.

5. A compound of claim 4 wherein said alkyl is n-$C_{11}H_{23}$.

6. A method of treating Parkinson's disease which comprises administering to a patient suffering from Parkinson's disease an effective amount of a compound of claim 1 for the treatment of Parkinson's disease.

7. A method of claim 6, wherein said effective amount is from 0.100 to 8 gm per day.

8. A method of claim 6 wherein $R_2$ is n-$C_{11}H_{23}$ alkyl.

9. A pharmaceutical composition for the treatment of Parkinson's disease in dosage unit form suitable for oral administration which comprises from 0.100 to 0.800 gm of a compound of claim 1 and a pharmaceutically acceptable carrier therefor.

10. A pharmaceutical composition of claim 9 wherein $R_2$ is n-$C_{11}H_{23}$ alkyl.